United States Patent [19]
Höök et al.

[11] Patent Number: 5,789,549
[45] Date of Patent: Aug. 4, 1998

[54] FIBRONECTIN BINDING PROTEIN

[75] Inventors: Magnus Höök, Birmingham, Ala.;
Kjell Martin Lindberg, Uppsala,
Sweden; Per-Eric Lindgren, Uppsala,
Sweden; Lars Christer Signäs,
Uppsala, Sweden

[73] Assignee: Alfa Laval Agri International Aktiebolag, Tumba, Sweden

[21] Appl. No.: 729,766

[22] Filed: Oct. 7, 1996

Related U.S. Application Data

[62] Division of Ser. No. 428,713, Apr. 25, 1995, which is a division of Ser. No. 125,222, Sep. 23, 1993, Pat. No. 5,416,021, which is a continuation of Ser. No. 973,551, Nov. 9, 1992, abandoned, which is a continuation of Ser. No. 352,949, May 17, 1989, abandoned.

[30] Foreign Application Priority Data

May 20, 1988 [SE] Sweden ................................ 8801894

[51] Int. Cl.$^6$ ................ C07K 5/00; C07K 14/00; C12N 15/11; C07H 21/04
[52] U.S. Cl. ............ 530/350; 530/300; 530/825; 435/69.1; 435/253.4; 435/252.33; 536/23.1; 536/23.4; 536/23.5
[58] Field of Search ................ 530/300, 350, 530/825; 435/252.33, 253.4, 69.1; 536/23.1, 23.4, 23.5

*Primary Examiner*—Paula K. Hutzell
*Assistant Examiner*—Khalid Masood
*Attorney, Agent, or Firm*—Burns, Doane, Swecker & Mathis, L.L.P.

[57] ABSTRACT

The present invention relates to new recombinant DNA-molecules comprising nucleotide sequences of *S. dysgalactiae* encoding for at least one protein or polypeptide having fibronectin binding property.

13 Claims, 8 Drawing Sheets

FIG. 3A pSDF102

```
A1  EDTQTSQEDI V-LGGPGQVI DFTEDSQPGM SGNNSHTT
    ||   ||||  |  || |||| ||||| | || || ||||
A2  EDSKPSQEDE VIIGGQGQVI DFTEDTQSGM SGDNSHTDG TVLE
    |||||||||| |||||||||| |||||| || ||
A3  EDSKPSQEDE VIIGGQGQVI DFTEDTQTGM SGAGQVESP
     |  ||||   ||  |||  ||  ||    |
    TITEETHKPE IIMGGQSDPI DMVEDTLPGM SGSNEAEDT
```

FIG. 3B pSDF203

```
A1  EETLPTEQGQ SGSTTEVEDT KGPEVIIGGQ GEIVDI
    || |||||||  |||||||| ||||||||||  || |||
A2  EENLPTEQGQ SGSTTEVEDT KGPEVIIGGQ GEVVDI
    || |||||||| ||||||||  |       |
A3  EESLPTEQGQ SGSTTEVEDS KPKLSIHFDN EWPKED
```

FIG. 4

```
1    ----------+--   -------+----   -----+------   ---+--------  48
     CTAGATACCTCA  GAAAACAAAAAA  TCTGTAACTGAA  AAAGTAATAACT
     LeuAspThrSer  GluAsnLysLys  SerValThrGlu  LysValIleThr
49   -+---------+   ---------+--   -------+----   -----+------  96
     AGCGATGTTAAA  TATAAGATTAAT  GATAAAGAAGTG  AAAGGTAAAGAA
     SerAspValLys  TyrLysIleAsn  AspLysGluVal  LysGlyLysGlu
97   ---+--------   -+---------+   ----------+--   -------+----  144
     CTAGACGATGTC  TCTTTAACTTAC  AGTAAAGAAACC  GTTCGTAAGCCA
     LeuAspAspVal  SerLeuThrTyr  SerLysGluThr  ValArgLysPro
145  -----+------   ---+--------   -+---------+   ---------+--  192
     CAGGTGGAACCA  AATGTTCCTGAT  ACACCTCAGGAA  AAACCATTGACA
     GlnValGluPro  AsnValProAsp  ThrProGlnGlu  LysProLeuThr
193  --------+----  -----+------  ---+--------  -+---------+   240
     CCGCTTGCACCG  TCAGAACCTTCA  CAACCATCTATT  CCAGAGACACCA
     ProLeuAlaPro  SerGluProSer  GlnProSerIle  ProGluThrPro
241  ----------+--  -------+----  -----+------  ---+--------   288
     CTGATACCGTCA  GAACCTTCAGTT  CCAGAGACATCA  ACACCAGAAGGT
     LeuIleProSer  GluProSerVal  ProGluThrSer  ThrProGluGly
289  -+---------+   ---------+--   -------+----   -----+------  336
     CCAACAGAGGGA  GAAAATAATCTT  GGTGGTCAGAGT  GAAGAGATAACG
     ProThrGluGly  GluAsnAsnLeu  GlyGlyGlnSer  GluGluIleThr
337  ---+--------   -+---------+   ----------+--   -------+----  384
     ATTACAGAAGAT  TCTCAATCAGGG  ATGTCTGGTCAA  AATCCTGGTTCT
     IleThrGluAsp  SerGlnSerGly  MetSerGlyGln  AsnProGlySer
385  -----+------   ---+--------   -+---------+   ---------+--  432
     GGAAATGAAACA  GTGGTTGAAGAC  ACTCAAACAAGT  CAAGAGGATATT
     GlyAsnGluThr  ValValGluAsp  ThrGlnThrSer  GlnGluAspIle
433  --------+----  -----+------  ---+--------  -+---------+   480
     GTACTTGGTGGT  CCAGGTCAAGTG  ATTGACTTTACA  GAAGATAGCCAA
     ValLeuGlyGly  ProGlyGlnVal  IleAspPheThr  GluAspSerGln
481  ----------+--  -------+----  -----+------  ---+--------   528
     CCGGGTATGTCT  GGTAATAATAGC  CATACTATTACA  GAAGATTCTAAA
     ProGlyMetSer  GlyAsnAsnSer  HisThrIleThr  GluAspSerLys
529  -+---------+   ---------+--   -------+----   -----+------  576
     CCAAGTCAAGAG  GATGAGGTGATA  ATCGGCGGTCAA  GGTCAGGTGATT
     ProSerGlnGlu  AspGluValIle  IleGlyGlyGln  GlyGlnValIle
577  ---+--------   -+---------+   ----------+--   -------+----  624
     GACTTTACAGAA  GATACTCAATCT  GGTATGTCTGGG  GATAATAGCCAT
     AspPheThrGlu  AspThrGlnSer  GlyMetSerGly  AspAsnSerHis
625  -----+------   ---+---+----   -+---------+   ---------+--  672
     ACAGATGGGACA  GTGCTTGAAGAA  GACTCTAAACCA  AGTCAAGAGGAT
     ThrAspGlyThr  ValLeuGluGlu  AspSerLysPro  SerGlnGluAsp
673  --------+----  -----+------  ---+--------  -+---------+   720
     GAGGTGATAATC  GGCGGTCAAGGT  CAAGTGATTGAC  TTTACAGAAGAT
     GluValIleIle  GlyGlyGlnGly  GlnValIleAsp  PheThrGluAsp
```

FIG. 4

```
721 ----------+-- -------+---- -----+------ ---+--------- 768
    ACCCAAACCGGT ATGTCTGGGGCT GGACAAGTAGAG AGTCCAACAATC
    ThrGlnThrGly MetSerGlyAla GlyGlnValGlu SerProThrIle
769 -+---------+ ----------+-- --------+---- -----+------ 816
    ACCGAAGAAACC CATAAACCAGAA ATAATCATGGGC GGTCAAAGTGAC
    ThrGluGluThr HisLysProGlu IleIleMetGly GlyGlnSerAsp
817 ---+--------- -+----------+ ----------+-- --------+---- 864
    CCTATTGATATG GTTGAGGACACT CTTCCTGGTATG TCTGGCTCTAAT
    ProIleAspMet ValGluAspThr LeuProGlyMet SerGlySerAsn
865 -----+------ ---+-------- -+----------+ ----------+-- 912
    GAAGCTACTGTT GTGGAAGAAGAC ACACGTCCTAAA CTTCAATTCCAT
    GluAlaThrVal ValGluGluAsp ThrArgProLys LeuGlnPheHis
913 --------+---- -----+------ ---+--------- -+---------+ 960
    TTTGATAATGAA GAGCCCGTTCCT GCAACGGTTCCA ACCGTTTCTCAA
    PheAspAsnGlu GluProValPro AlaThrValPro ThrValSerGln
961 ----------+-- -------+---- -----+------ ---+--------- 1008
    ACTCCTATTGCT CAGGTAGAAAGT AAAGTGCCTCAT GCCAAAGCAGAG
    ThrProIleAla GlnValGluSer LysValProHis AlaLysAlaGlu
1009 -+---------+ ----------+-- --------+---- -----+------ 1056
    AGTGCGTTACCT CAAACTGGAGAT ACAAATAAACTA GAAACGTTCTTT
    SerAlaLeuPro GlnThrGlyAsp ThrAsnLysLeu GluThrPhePhe
1057 ---+--------- -+----------+ ----------+-- --------+---- 1104
    ACCATTACAGCA CTAACTGTTATT GGAGCGGCAGGA TTACTAGGCAAA
    ThrIleThrAla LeuThrValIle GlyAlaAlaGly LeuLeuGlyLys
1105 -----+------ ---+--------- -+----------+ ----------+-- 1152
    AAACGTCGTAAT AATCAAACTGAT TAATCAGCAGAT TTCATCAAACGC
    LysArgArgAsn AsnGlnThrAsp EndSerAlaAsp PheIleLysArg
1153 --------+---- -----+------ ---+--------- -+---------+ 1200
    TATAAACAAGGC TAACATTTTAGC CTTGTTTTATAT TGTTTCACTGAC
    TyrLysGlnGly End
1201 ----------+-- -------+---- -----+------ ---+--------- 1248
    CTCTAAAAGTTA TGACTGTTTTAA AGGGGGGGTAGG CCAATCCTCAAA
1249 -+---------+ ----------+-- --------+---- -----+------ 1296
    AGTAGTTAAGTT GAGAAACACCAC ATCACTTTAGTC TTACTGCGCATA
1297 ---+--------- -+----------+ ----------+-- --------+---- 1344
    CTAAAAGCAAAA GATAATTAGGAG CACTTGCTAACT GGAAAAAATCAA
1345 -----+------ ---+--------- -+---- 1374
    ATGCAAAGCTAG TTGCCAAAGAAC TCTAGA
```

FIG. 5

```
1   ------------+---  --------+----  -----+------  ---+--------  48
    CTCGAGGAAACT TTGCCAACAGAG GAACATCAATCA GGTGATACCACA
    LeuGluGluThr LeuProThrGlu GluHisGlnSer GlyAspThrThr
49  -+----------+  ----------+--  --------+----  -----+------  96
    ACTATTGAAGAT ACTCGCCCGATT GATACCATGTCA GGTCTATCAGGA
    ThrIleGluAsp ThrArgProIle AspThrMetSer GlyLeuSerGly
97  ---+--------  -+----------+  ----------+--  -------+----  144
    GAGACTGGGCAG TCTGGTAATACT ACAATTGAGGAA GATAGTACGACT
    GluThrGlyGln SerGlyAsnThr ThrIleGluGlu AspSerThrThr
145 ------+------  ---+--------  -+----------+  ---------+--  192
    CACGTTAAATTC TCAAAACGTGAT ATTAATGGTAAA GAACTAGCAGGT
    HisValLysPhe SerLysArgAsp IleAsnGlyLys GluLeuAlaGly
193 --------+----  -----+------  ---+--------  -+----------+  240
    GCTATGATTGAA CTACGTAATCTA TCAGGTCAAACT ATTCAATCATGG
    AlaMetIleGlu LeuArgAsnLeu SerGlyGlnThr IleGlnSerTrp
241 ----------+--  --------+----  -----+------  ---+--------  288
    ATATCAGACGGC ACAGTTAAAGTT TTCTACTTGATG CCAGGGACTTAT
    IleSerAspGly ThrValLysVal PheTyrLeuMet ProGlyThrTyr
289 -+----------+  ----------+--  --------+----  -----+------  336
    CAATTTGTGGAG ACGGCAGCGCCA GAAGGTTATGAA TTGGCAGCTCCA
    GlnPheValGlu ThrAlaAlaPro GluGlyTyrGlu LeuAlaAlaPro
337 ---+--------  -+----------+  ----------+--  -------+----  384
    ATTACCTTCACA ATTGATGAGAAA GGACAAATTTGG GTAGACAGTACA
    IleThrPheThr IleAspGluLys GlyGlnIleTrp ValAspSerThr
433 --------+----  -----+------  ---+--------  -+----------+  480
    ATTACTGAGGCG AGTCAATCTATT GATTTCGAGGAA ACTTTACCAACT
    IleThrGluAla SerGlnSerIle AspPheGluGlu ThrLeuProThr
481 ----------+--  --------+----  -----+------  ---+--------  528
    GAACAAGGCCAA TCTGGCTCTACA ACGGAGGTTGAG GATACTAAAGGC
    GluGlnGlyGln SerGlySerThr ThrGluValGlu AspThrLysGly
529 -+----------+  ----------+--  --------+----  -----+------  576
    CCAGAAGTCATT ATCGGCGGTCAG GGAGAGATTGTT GATATCGAGGAG
    ProGluValIle IleGlyGlyGln GlyGluIleVal AspIleGluGlu
577 ---+--------  -+----------+  ----------+--  -------+----  624
    AACTTACCAACT GAACAAGGCCAA TCTGGCTCTACA ACTGAAGTAGAG
    AsnLeuProThr GluGlnGlyGln SerGlySerThr ThrGluValGlu
625 ------+------  ---+--------  -+----------+  ---------+--  672
    GATACTAAAGGC CCAGAAGTCATT ATCGGCGGTCAA GGAGAGGTTGTT
    AspThrLysGly ProGluValIle IleGlyGlyGln GlyGluValVal
673 --------+----  -----+------  ---+--------  -+----------+  720
    GATATTGAGGAG AGCTTACCAACT GAACAAGGCCAA TCTGGCTCTACA
    AspIleGluGlu SerLeuProThr GluGlnGlyGln SerGlySerThr
721 ----------+--  --+----+----  -----+------  ---+--------  768
    ACTGAAGTAGAA GATAGCAAGCCT AAACTCTCTATC CACTTTGATAAC
    ThrGluValGlu AspSerLysPro LysLeuSerIle HisPheAspAsn
```

FIG. 5

```
769 -+---------+  ---------+--  -------+----  -----+------ 816
    GAGTGGCCTAAG GAAGACAAACCA CAACTACCTGCC GTTGAAAAACCT
    GluTrpProLys GluAspLysPro GlnLeuProAla ValGluLysPro
817 ---+--------  -+---------+  ---------+--  -------+---- 864
    AAGACTAAGGAG AGCTTGCCAGCC GCAGGGGAAGCT GAACATGTCTTA
    LysThrLysGlu SerLeuProAla AlaGlyGluAls GluHisValLeu
865 -----+------  ---+-------- 888
    TCTACTATCGTG GGAGCAATGATC
    SerThrIleVal GlyAlaMetIle
```

FIBRONECTIN BINDING PROTEIN

This application is a divisional of application Ser. No. 08/428,713, filed Apr. 25, 1995, which is a divisional of Ser. No. 08/125,222, filed Sep. 23, 1993, now U.S. Pat. No. 5,416,021, which is a continuation of Ser. No. 07/973,551, (abandoned) filed Nov. 9, 1992, which is a continuation of Ser. No. 07/352,949, (abandoned) filed May 17, 1989.

DESCRIPTION

1. Technical Field

The present invention relates to fibronectin binding proteins and hybrid-DNA molecules, e.g., plasmids or phages containing at least one nucleotide sequence encoding for said proteins. Further the invention relates to microorganisms containing such molecules and their use to produce said proteins, and the synthetic production of said proteins.

The object of the present invention is to obtain minimal fibronectin binding proteins.

A further object of the present invention is to obtain said proteins by means of genetic engineering technique using e.g., a plasmid containing a nucleotide sequence encoding for the proteins.

A further object of the present invention is to obtain a possibility to prepare said proteins by means of chemical synthesis.

2. Background of the Invention

WO-A1-85/05553 discloses bacterial cell surface proteins having fibronectin, fibrinogen, collagen, and/or laminin binding ability. Thereby it is shown that different bacteria have an ability to bind to fibronectin, fibrinogen, collagen and/or laminin. It is further shown that fibronectin binding protein from Staphylococcus aureus has a molecular weight of 165 kD, and/or 87 kD, whereby it is probable that the smaller protein is a part of the larger one.

Fibronectin is a large glycoprotein having a molecular weight of about 450 kD and having two similar subunits, which can have varying molecular sizes depending on a complex splicing pattern of the precursor mRNA. The protein is present in basement membranes, and connective tissue, but also in a soluble form in different body fluids, such as blood plasma (1). After the original discovery by Kuusela in 1978 that *S. aureus* binds to fibronectin (2) it has been shown that certain strains of other pathogenic bacteria, such as streptococci of different serological types (3), *E. coli* (4) and Salmonella (5) can bind to this protein (6).

Adhesion of pathogenic bacteria to surfaces is today a generally recognized concept in the discussions of wound pathogens using surface receptors to bind to different proteins on epithelium cell surfaces, in connective tissue matrix, and in wound crusts, such as e.g., fibronectin, fibrinogen, collagen and laminin. The problem is that these receptors are present in a relatively small amount on the bacterial cell surface, and that they are difficult to release. One feasible way in cases the receptors consist of proteins is to clone the genes for the receptors in question to be able to prepare them in quantities which makes it considerably easier to study infections and the course of infections as well as prophylactical and therapeutical treatment of infections by wound pathogens.

Screening studies of different serological groups of streptococci, such as A, C, and G according to Lancefield (3) have shown that the strains tested can bind to different connective tissue proteins such as fibronectin, fibrinogen, collagen and laminin and different immunoglobulins (7,8) to a varying degree and with different specificity.

In order to further characterize fibronectin binding proteins from streptococci, particularly genes from *Streptococcus dysgalactiae* for such proteins have been cloned in *E. coli*. The fibronectin binding domains of these proteins have also been localized and properties and functions of proteins containing these domains will be discussed below.

DESCRIPTION OF THE PRESENT INVENTION

It has now surprisingly been shown possible to obtain hybrid-DNA molecules comprising nucleotide sequences of the genes coding for proteins or polypeptides having fibronectin binding properties. As evident from the below the following nucleotide sequences are present in the plasmides, pSDF102, and pSDF203, respectively, which encode said proteins.

```
CTA GAT ACC TCA GAA AAC AAA AAA TCT GTA ACT GAA AAA GTA ATA ACT
AGC GAT GTT AAA TAT AAG ATT AAT GAT AAA GAA GTG AAA GGT AAA GAA
CTA GAC GAT GTC TCT TTA ACT TAC AGT AAA GAA ACC GTT CGT AAG CCA
CAG GTG GAA CCA AAT GTT CCT GAT ACA CCT CAG GAA AAA CCA TTG ACA
CCG CTT GCA CCG TCA GAA CCT TCA CAA CCA TCT ATT CCA GAG ACA CCA
CTG ATA CCG TCA GAA CCT TCA GTT CCA GAG ACA TCA ACA CCA GAA GGT
CCA ACA GAG GGA GAA AAT AAT CTT GGT GGT CAG AGT GAA ATA ACG ATT
ACA GAA GAT TCT CAA TCA GGG ATG TCT GGT CAA AAT CCT GGT TCT GGA
AAT GAA ACA GTG GTT

GAA GAC ACT CAA ACA AGT CAA GAG GAT ATT GTA CTT GGT GGT CCA GGT
CAA GTG ATT GAC TTT ACA GAA GAT AGC CAA CCG GGT ATG TCT GGT AAT
AAT AGC CAT ACT ATT ACA

GAA GAT TCT AAA CCA AGT CAA GAG GAT GAG GTG ATA ATC GGC GGT CAA
```

-continued

```
GGT CAG GTG ATT GAC TTT ACA GAA GAT ACT CAA TCT GGT ATG TCT GGG
GAT AAT AGC CAT ACA GAT GGG ACA GTG CTT GAA

GAA GAC TCT AAA CCA AGT CAA GAG GAT GAG GTG ATA ATC GGC GGT CAA
GGT CAA GTG ATT GAC TTT ACA GAA GAT ACC CAA ACC GGT ATG TCT GGG
GCT GGA CAA GTA GAG AGT CCA ACA ACT ACC GAA GAA ACC CAT AAA CCA
GAA ATA ATC ATG GGC GGT CAA AGT GAC CCT ATT GAT ATG GTT GAG GAC
ACT CTT CCT GGT ATG TCT GGC TCT AAT GAA GCT ACT GTT GTG GAA GAA
GAC ACA CGT CCT AAA CTT CAA TTC CAT TTT GAT AAT GAA GAG CCC GTT
CCT GCA ACG GTT CCA ACC GTT TCT CAA ACT CCT ATT GCT CAG GTA GAA
AGT AAA GTG CCT CAT GCC AAA GCA GAG AGT GCG TTA CCT CAA ACT GGA
GAT ACA AAT AAA CTA GAA ACG TTC TTT ACC ATT ACA GCA CTA ACT GTT
ATT GGA GCG GCA GGA TTA CTA GGC AAA AAA CGT CGT AAT AAT CAA ACT
GAT TAA TCA GCA GAT TTC ATC AAA CGC TAT AAA CAA GGC TAA CAT TTT
AGC CTT GTT TTA TAT TGT TTC ACT GAC CTC TAA AAG TTA TGA CTG TTT
TAA AGG GGG GGT AGG CCA ATC CTC AAA AGT AGT TAA GTT GAG AAA CAC
CAC ATC ACT TTA GTC TTA CTG CGC ATA CTA AAA GCA AAA GAT AAT TAG
GAG CAG TTG CTA ACT GGA AAA AAT CAA ATG CAA AGC TAG TTG CCA AAG
AAC TCT AGA
``` and/or

```
CTC GAG GAA ACT TTG CCA AAC GAG GAA CAT CAA TCA GGT GAT ACC ACA
ACT ATT GAA GAT ACT CGC CCG ATT GAT ACC ATG TCA GGT CTA TCA GGA
GAG ACT GGG CAG TCT GGT AAT ACT ACA ATT GAG GAA GAT AGT ACG ACT
CAC GTT AAA TTC TCA AAA CGT GAT ATT AAT GGT AAA GAA CTA GCA GGT
GCT ATG ATT GAA CTA CGT AAT CTA TCA GGT CAA ACT ATT CAA TCA TGG
ATA TCA GAC GGC ACA GTT AAA GTT TTC TAC TTG ATG CCA GGG ACT TAT
CAA TTT GTG GAG ACG GCA GCG CCA GAA GGT TAT GAA TTG GCA GCT CCA
ATT ACC TTC ACA ATT GAT GAG AAA GGA CAA ATT TGG GTA GAC AGT ACA
ATT ACT GAG GCG AGT CAA TCT ATT GAT TTC
```

```
GAG GAA ACT TTA CCA ACT GAA CAA GGC CAA TCT GGC TCT ACA ACG GAG
GTT GAG GAT ACT AAA GGC CCA GAA GTC ATT ATC GGC GGT CAG GGA GAG
ATT GTT GAT ATC
```

```
GAG GAG AAC TTA CCA ACT GAA CAA GGC CAA TCT GGC TCT ACA ACT GAA
GTA GAG GAT ACT AAA GGC CCA GAA GTC ATT ATC GGC GGT CAA GGA GAG
GTT GTT GAT ATT
```

```
GAG GAG AGC TTA CCA ACT GAA CAA GGC CAA TCT GGC TCT ACA ACT GAA
GTA GAA GAT
```

Figure 3A:
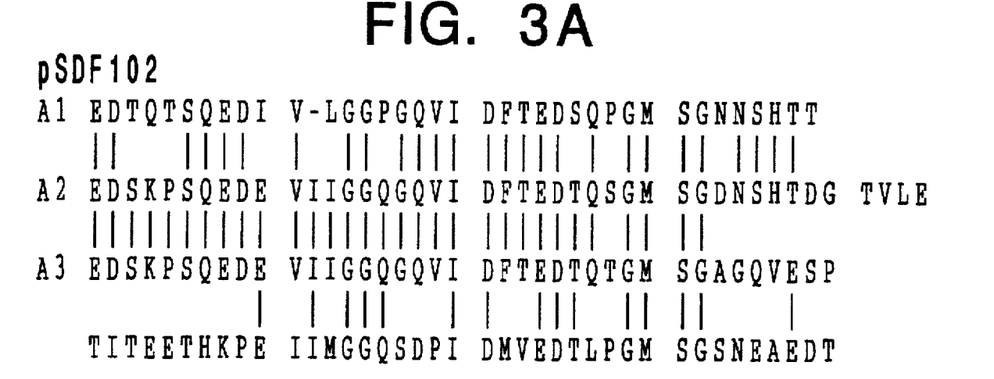
FIGS. 3A and B show repetitive sequences of pSDF102 och pSDF203.
Figure 3B:
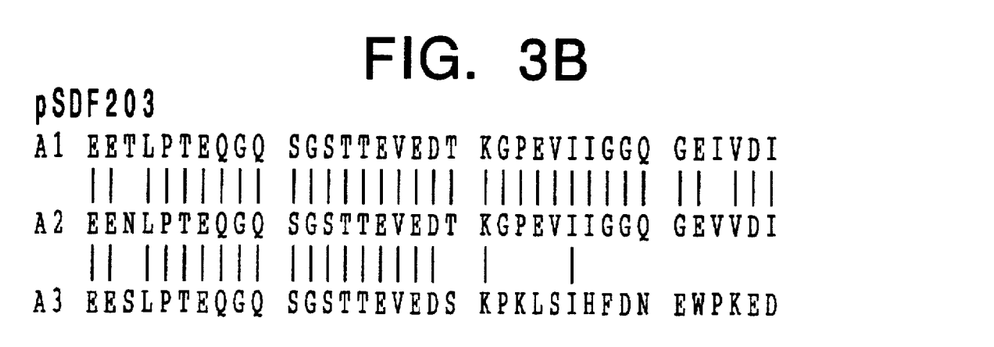

```
AGC AAG CCT AAA CTC TCT ATC CAC TTT GAT AAC GAG TGG CCT AAG GAA
GAC AAA CCA CAA CTA CCT GCC GTT GAA AAA CCT AAG ACT AAG GAG AGC
TTG CCA GCC GCA GGG GAA GCT GAA CAT GTC TTA TCT ACT ATC GTG GGA
GCA ATG ATC
``` whereby the smaller repetitive regions (cf. FIG. 3) in each gene above code for the peptides having fibronectin binding activity.

The invention further comprises a plasmid or phage comprising a nucleotide sequence coding for said fibronectin binding proteins.

The invention further comprises micro-organisms containing at least one hydrid-DNA molecule according to above. Such micro-organisms have been deposited at the Deutsche Sammlung von Mikroorganismen under deposition number DSM 4614 (pSDF102) and DSM 4613 (pSDF203).

The invention further relates to a process for preparing fibronectin binding proteins comprising transfer of at least one hybrid-DNA molecule according to above into a micro-organism, cultivating the said micro-organism in a culture medium, and isolating the protein thus formed in a manner known per se.

A further aspect of the present invention comprises a chemical synthesis of the fibronectin binding proteins, whereby amino acids connected into peptides in which the order of amino acids is based upon said nucleotide sequences encoding said proteins. The synthesis starts from the C-terminal glycine, and aspartic acid, respectively, which are reacted stepwise with the appropriate amino acid, whereby they are finally reacted with glutamic acid, and glutamic acid, respectively, at the N-terminal end to the formation of the fibronectin binding peptide regions.

Appropriate amino acids can also be fused to said amino acid sequence such as the IgG binding region of protein A. The invention will be described more in detail in the following with reference to the Examples given, however, without being restricted thereto.

EXAMPLE 1

Construction of a gene bank of chromosomal DNA from Streptococcus dysgalactiae Chromosomal DNA from *Streptococcus dysgalactiae*, strain S2, was prepared in accordance with the perchlorate method (9). The DNA was partially cleaved using Sau 3AI, was size fractionated on a 1% agarose gel, and the DNA fragment within the size range 3 to 9 kb were collected, electro eluated, and purified on a Nensorb (Du Pont) column.

The plasmid vector pUC18 was cleaved using Bam HI and was phosphatase treated. The partially cleaved and fractionated streptococcus-DNA was ligated with the cleaved pUC18 vector. The ligation mixture was transformed to freeze competent *E. coli*, strain TG1, and was spred on LA plates containing ampicillin (50 µg/ml) and IPTG (0.1 mM), and 0.004% X-gal, called axi-plates. White colonies were transferred to LA plates with ampicillin (50 µg/ml).

Screening of a gene bank for a fibronectin binding protein (FNBP)

The white colonies from the axi plates were picked using tooth picks to LA plates with ampicillin. 52 colonies per plate. In total 728 transformants were collected. These were screened with regard to fibronectin binding activity using a filter assay method according to below.

Transformants are picked from an axi-plates to LA plates with ampicillin, and the plates are incubated over night. From these plates the colonies are replicated over to new LA plates, and which are incubated at 37° C. over night. A nitro-cellulose filter is put onto each agarplate with grown out colonies. When the filters are completely moistened the colonies are attached by suction and the filters are carefully removed. The filters are exposed to chloroform vapour for 5 min, and are then washed, 3×10 min, 37° C. in a buffer solution consisting of 100 mM Tris-HCl pH 7.5, 0.05% Tween-40, and 150 mM NaCl. The filters are allowed to dry at room temperature for about 30 min. The filters are preincubated in 150 mM NaCl, 10 mM Tris-HCl pH 7.5, and 1.4% fat free milk powder, for 2 hrs at 37° C., or room temperature over night. The milk powder buffer has to be freshly prepared. $^{125}$I labelled fibronectin is added (about 30,000 cpm per filter), and the filters are incubated at room temperature over night. The filters are washed, 3×10 min at 37° C. using a solution of 0.05% Tween-40, and 150 mM NaCl, whereupon the filters are dried. An unexposed film is put thereon, and is exposed for 3 to 5 days. The film is developed and the clones which have bound to $^{125}$I-fibronectin are identified and isolated.

The filter screening assay showed 3 positive clones, which all were further analysed. The fibronectin binding ability was further determined in a competition assay (10). Lysate of the *E. coli* clones were prepared by lysing the bacteria using lysozyme (1 mg/ml) in a buffer solution consisting of 100 mM Tris-HCl pH 7.5, 150 mM NaCl, and 1 mM EDTA. The fibronectin binding acti-vity was analysed by determining the ability of the lysates to compete with *S. aureus*, strain Cowan I (alternatively strain 8325-4), and *S. dysgalactiae*, strain S2, respectively, with regard to their ability to bind to the $^{125}$I-labelled 29 kD fragment of fibronectin. The test showed that it is possible to drive out the fibronectin binding to the two staphylococcal strains, as well as strain S2 of *S. dysgalactiae* when using lysates of *E. coli* clones containing the strepto-cocci DNA. Inversely the binding of the 29 kD fragment of fibronectin to *S. dysgalactiae* can be inhibited by adding a lysate of *E. coli* clone containing a gene for fibronectin binding protein of *S. aureus*.

Restriction mapping and subcloning

Plasmid-DNA of the three positive subclones from the filter assay, called pSDF100, pSDF200, and pSDF300 were prepared using the LiCl method (11) and determined to be 4.9 kb, 6.9 kb, and 6.5 kb, respectively, by cleavages using restriction enzymes and analysis on agarose gels. All three clones were cleaved using about 20 of the most common restriction enzymes, which recognizes a sequence of 6 nucleotides and starting from cleavage pattern restriction maps were drafted. Two of the clones, pSDF100, and pSDF300, were partly overlapping having a 3.9 kb sequence in common, and thus only one was selected for further studies. As pSDF100 had a higher fibronectin binding activity than pSDF300 the former was selected.

pSDF100 and pSDF200 were subcloned in order to identify more closely the regions encoding fibronectin binding activity. pSDF100 was cleaved using Bam HI, whereupon the plasmid was re-ligated. This clone with the Bam HI-Bam HI fragment deleted was called pSDF101 and was positive. pSDF101 was further cleaved using XbaI, which gave 3 fragments, one mainly consisting of the pUC18 vector,. The other two XbaI-XbaI fragments were purified and inserted into the pUC18 vector. One of these fragments encodes fibronectin binding activity. This clone was called pSDF102. In the corresponding way subclones were constructed from pSDF200. The ClaI-SacI fragment deleted from pSDF200 gave a clone called pSDF201, and further the BglII-EcoRI fragment eliminated from pSDF201 gives pSDF202.

Figure 1A:
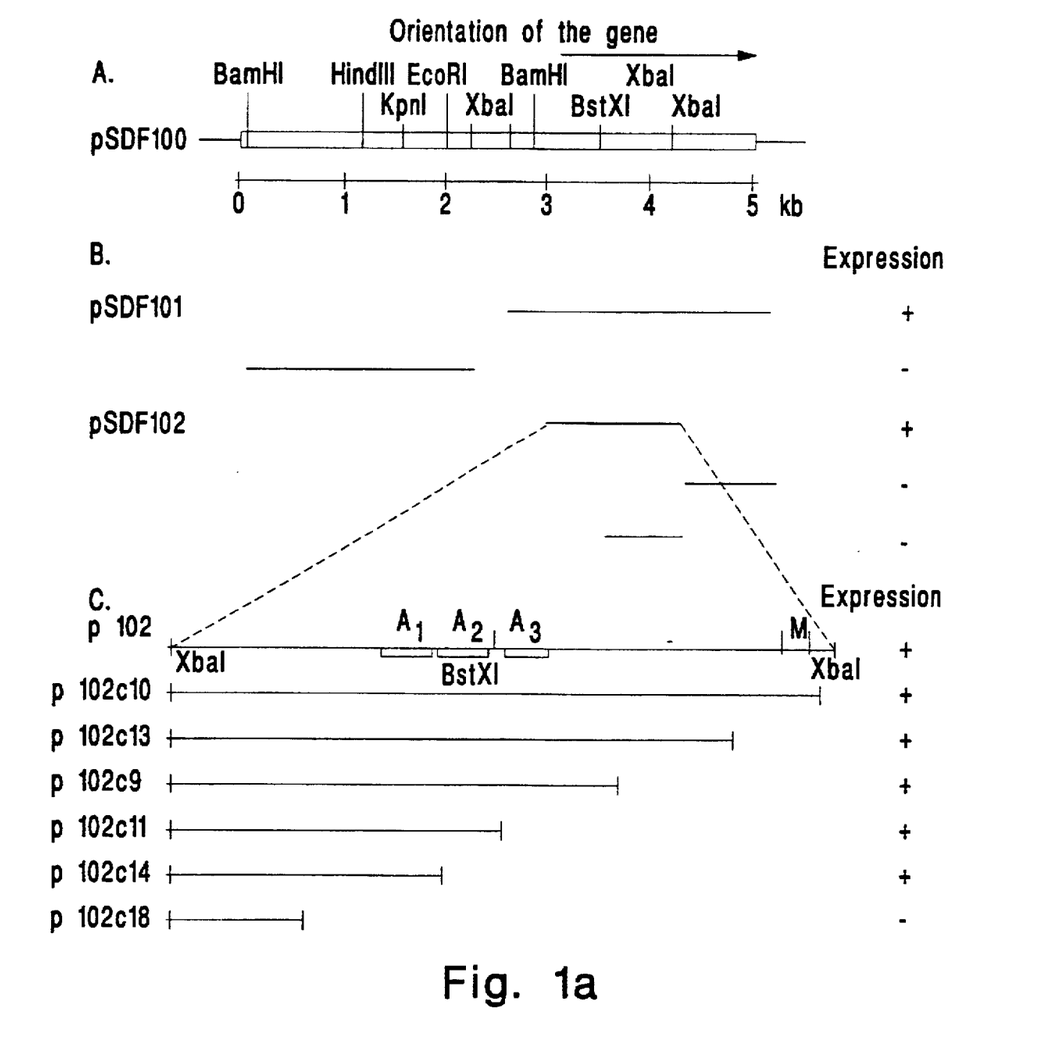
FIG. 1a. Restriction map and subclones of the 5 kb insert from *S. dysgalactiae* in the pUC18-vector called pSDF100.
Figure 1B:
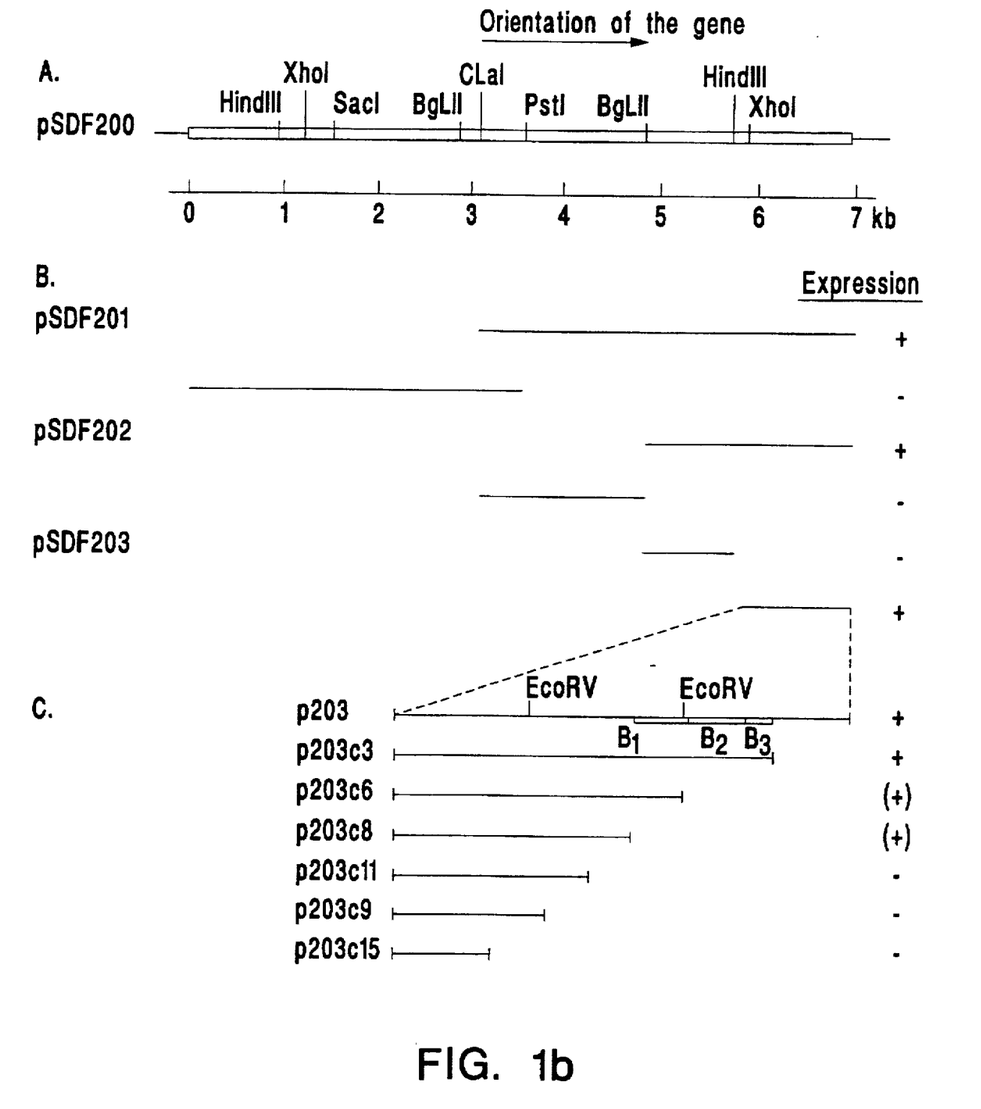
FIG. 1b. Restriction map and subclones of the 6.9 kb insert from *S. dysgalactiae* in the pUC18-vector called pSDF200.
Figure 2:
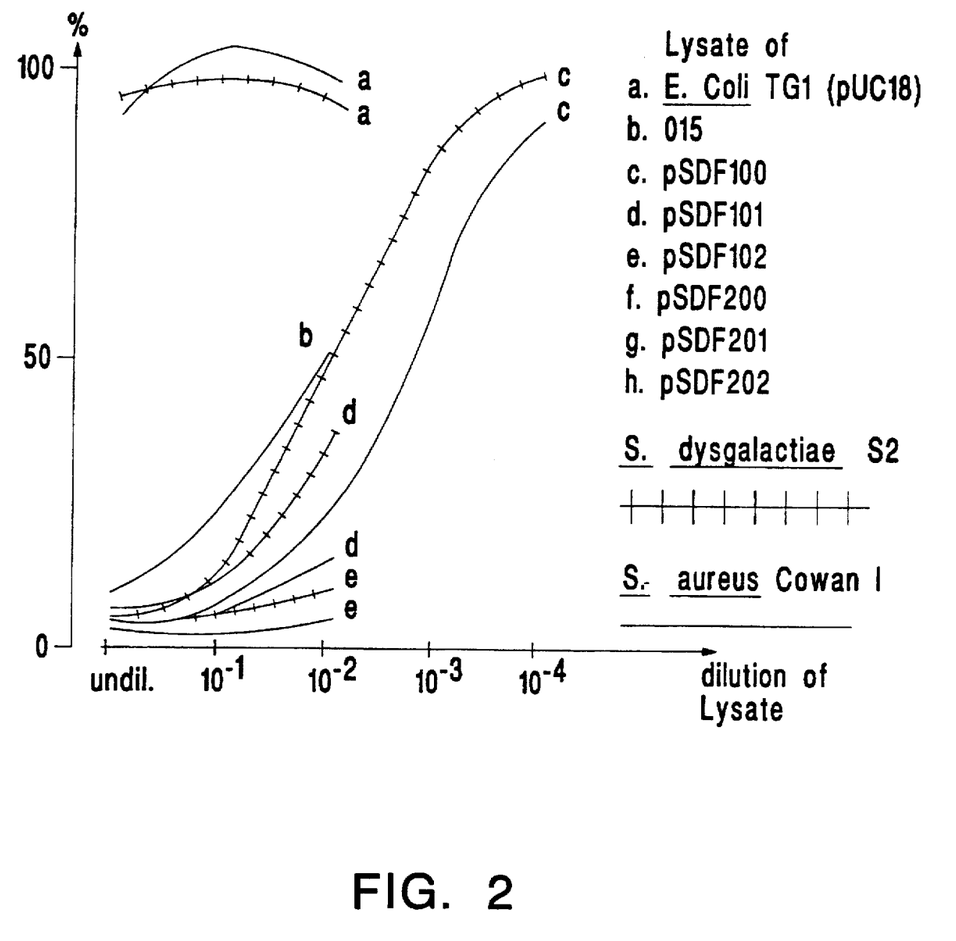
FIG. 2 Inhibition assay in tubes

Finally, the XhoI-EcoRI fragment has been deleted from pSDF202. This new clone was thereby obtained was called pSDF203. All these new subclones are positive, i.e., they express fibronectin binding activity, cf. FIG. 1a and FIG. 1b.

Further subcloning by EcoIII digestion

In order to facilitate the nucleotide sequencing according to the dideoxymethod smaller subclones differing 150 to 200 base pairs in length are required in order to obtain overlapping DNA sequence. Exonucleas III digest one of the DNA strands from the 5' overhang, or from the blunt end, but leaves the 3' overhang. The single stranded DNA is then digested using S1-nuclease. This technique is used in the "Erase-a-Base" System Kit (Promega, Madison, USA) and makes it possible to construct series of subclones which differs in some hundreds of nucleotides in size. In cases of interest the fibronectin binding activity was tested, cf. Table 1 below.

Table 1

Inhibition assay in tubes

Assay mixture: 100 µl of lysate of E. coli clones containing streptococcal DNA clones (the bacteria were grown on LB+50 µg ampicillin+1 mM IPTG, washed, and concentrated to $OD_{540}$=5.0) 100 µl Cowan I cells, heat killed, $OD_{540}$=5.0 100 µl $^{125}$I labelled fibronectin, 8865 cpm 200 µl PBS+0.1% BSA Incubation: 2 hrs, room temperature
Washing: Twice in PBS+0.1% BSA+0.05% Tween
The results are evident from Table 1 below.

| Lysate of subclone | Dilution of lysate | Number of cpm | % binding in relation to control without lysate |
|---|---|---|---|
| Control | Without lysate | 4430 | 100 |
| pSDF102c10 | undil | 550 | 12.4 |
| | $10^{-2}$ | 3870 | 87.4 |
| pSDF102c13 | undil | 200 | 4.5 |
| | $10^{-2}$ | 1440 | 32.5 |
| pSDF102c9 | undil | 610 | 13.8 |
| | $10^{-2}$ | 3170 | 71.6 |
| pSDF102c11 | undil | 1400 | 31.6 |
| | $10^{-2}$ | 3490 | 78.8 |
| pSDF102c14 | undil | 630 | 14.2 |
| | $10^{-2}$ | 3220 | 72.7 |

-continued

| Lysate of subclone | Dilution of lysate | Number of cpm | % binding in relation to control without lysate |
|---|---|---|---|
| pSDF102c18 | undil | 4030 | 91.0 |
| | $10^{-2}$ | 4300 | 97.1 |
| pSDF203c3 | undil | 640 | 14.4 |
| | $10^{-2}$ | 2780 | 62.8 |
| pSDF203c6 | undil | 2710 | 61.2 |
| | $10^{-2}$ | 4790 | 108 |
| pSDF203c8 | undil | 3180 | 71.8 |
| | $10^{-2}$ | 3660 | 82.6 |
| pSDF203c11 | undil | 3540 | 79.9 |
| | $10^{-2}$ | 3970 | 89.6 |
| pSDF203c15 | undil | 3860 | 87.1 |
| | $10^{-2}$ | 4300 | 97.1 |
| pSDF203c9 | undil | 4020 | 90.7 |
| | $10^{-2}$ | 4730 | 107 |
| pSDF102 | undil | 200 | 4.5 |
| | $10^{-2}$ | 1050 | 23.7 |
| PSDF203 | undil | 180 | 4.1 |
| | $10^{-2}$ | 950 | 21.4 |
| TG1 | undil | 3690 | 83.3 |

Nucleotide sequencing

Subclones obtained after an exoIII digestion and other subclones were sequenced using the dideoxy method according to Gem Seq$^R$ dsDNA Sequ-encing System (Promega Biotech., Madison, USA)

Nucleotide sequencing of pSDF102 gave the following sequence:

CTA GAT ACC TCA GAA AAC AAA AAA TCT GTA ACT GAA AAA GTA ATA ACT

AGC GAT GTT AAA TAT AAG ATT AAT GAT AAA GAA GTG AAA GGT AAA GAA

CTA GAC GAT GTC TCT TTA ACT TAC AGT AAA GAA ACC GTT CGT AAG CCA

CAG GTG GAA CCA AAT GTT CCT GAT ACA CCT CAG GAA AAA CCA TTG ACA

CCG CTT GCA CCG TCA GAA CCT TCA CAA CCA TCT ATT CCA GAG ACA CCA

CTG ATA CCG TCA GAA CCT TCA GTT CCA GAG ACA TCA ACA CCA GAA GGT

CCA ACA GAG GGA GAA AAT AAT CTT GGT GGT CAG AGT GAA ATA ACG ATT

ACA GAA GAT TCT CAA TCA GGG ATG TCT GGT CAA AAT CCT GGT TCT GGA

AAT GAA ACA GTG GTT

GAA GAC ACT CAA ACA AGT CAA GAG GAT ATT GTA CTT GGT GGT CCA GGT

```
CAA GTG ATT GAC TTT ACA GAA GAT AGC CAA CCG GGT ATG TCT GGT AAT
AAT AGC CAT ACT ATT ACA

GAA GAT TCT AAA CCA AGT CAA GAG GAT GAG GTG ATA ATC GGC GGT CAA
GGT CAG GTG ATT GAC TTT ACA GAA GAT ACT CAA TCT GGT ATG TCT GGG
GAT AAT AGC CAT ACA GAT GGG ACA GTG CTT GAA

GAA GAC TCT AAA CCA AGT CAA GAG GAT GAG GTG ATA ATC GGC GGT CAA
GGT CAA GTG ATT GAC TTT ACA GAA GAT ACC CAA ACC GGT ATG TCT GGG
GCT GGA CAA GTA GAG AGT CCA ACA ACT ACC GAA GAA ACC CAT AAA CCA
GAA ATA ATC ATG GGC GGT CAA AGT GAC CCT ATT GAT ATG GTT GAG GAC
ACT CTT CCT GGT ATG TCT GGC TCT AAT GAA GCT ACT GTT GTG GAA GAA
GAC ACA CGT CCT AAA CTT CAA TTC CAT TTT GAT AAT GAA GAG CCC GTT
GCT GCA ACG GTT CCA ACC GTT TCT CAA ACT CCT ATT GCT CAG GTA GAA
AGT AAA GTG CCT CAT GCC AAA GCA GAG AGT GCG TTA CCT CAA ACT GGA
GAT ACA AAT AAA CTA GAA ACG TTC TTT ACC ATT ACA GCA CTA ACT GTT
ATT GGA GCG GCA GGA TTA CTA GGC AAA AAA CGT CGT AAT AAT CAA ACT
GAT TAA TCA GCA GAT TTC ATC AAA CGC TAT AAA CAA GGC TAA CAT TTT
AGC CTT GTT TTA TAT TGT TTC ACT GAC CTC TAA AAG TTA TGA CTG TTT
TAA AGG GGG GGT AGG CCA ATC CTC AAA AGT AGT TAA GTT GAG AAA CAC
CAC ATC ACT TTA GTC TTA CTG CGC

-continued

```
GCT ATG ATT GAA CTA CGT AAT CTA TCA GGT CAA ACT ATT CAA TCA TGG
ATA TCA GAC GGC ACA GTT AAA GTT TTC TAC TTG ATG CCA GGG ACT TAT
CAA TTT GTG GAG ACG GCA GCG CCA GAA GGT TAT GAA TTG GCA GCT CCA
ATT ACC TTC ACA ATT GAT GAG AAA GGA CAA ATT TGG GTA GAC AGT ACA
ATT ACT GAG GCG AGT CAA TCT ATT GAT TTC

GAG GAA ACT TTA CCA ACT GAA CAA GGC CAA TCT GGC TCT ACA ACG GAG
GTT GAG GAT ACT AAA GGC CCA GAA GTC ATT ATC GGC GGT CAG GGA GAG
ATT GTT GAT ATC

GAG GAG AAC TTA CCA ACT GAA CAA GGC CAA TCT GGC TCT ACA ACT GAA
GTA GAG GAT ACT AAA GGC CCA GAA GTC ATT ATC GGC GGT CAA GGA GAG
GTT GTT GAT ATT

GAG GAG AGC TTA CCA ACT GAA CAA GGC CAA TCT GGC TCT ACA ACT GAA
GTA GAA GAT

AGC AAG CCT AAA CTC TCT ATC CAC TTT GAT AAC GAG TGG CCT AAG GAA
GAC AAA CCA CAA CTA CCT GCC GTT GAA AAA CCT AAG ACT AAG GAG AGC
TTG CCA GCC GCA GGG GAA GCT GAA CAT GTC TTA TCT ACT ATC GTG GGA
GCA ATG ATC
``` whereby the repetitve domains or the sequence

```
GAG GAA ACT TTA CCA ACT GAA CAA GGC CAA TCT GGC TCT ACA ACG GAG
GTT GAG GAT ACT AAA GGC CCA GAA GTC ATT ATC GGC GGT CAG GGA GAG
ATT GTT GAT ATC

GAG GAG AAC TTA CCA ACT GAA CAA GGC CAA TCT GGC TCT ACA ACT GAA
GTA GAG GAT ACT AAA GGC CCA GAA GTC ATT ATC GGC GGT CAA GGA GAG
GTT GTT GAT ATT

GAG GAG AGC TTA CCA ACT GAA CAA GGC CAA TCT GGC TCT ACA ACT GAA
GTA GAA GAT
``` encode a peptide having fibronectin binding activity.

Southern blot hybridisation detects no homologies on DNA level between the genes for the fibronectin binding protein of S. aureus, and the corresponding genes from S. dysgalactiae. The competitive inhibition between the proteins from the respective species depends most probably on the fact that their binding sites in the fibronectin within the NH$_2$ terminal 29 kD fragment are close to each other and thereby sterically block the binding.

Western blot analyses of lysate of the two fibronectin binding E. coli clones studied indicate using $^{125}$I labelled fibronectin and autoradiography shows that subclone pSDF203 encodes a protein having a molecular weight of 70 kDa, and subclone pSDF102 a corresponding protein having a molecular weight of 110 kD.

The deduced amino acid sequences of the proteins or polypeptides from the above given nucleotide sequences encode for are the following:

```
Glu Asp Thr Gln Thr Ser Gln Glu Asp Ile Val Leu Gly Gly Pro Gly
Gln Val Ile Asp Phe Thr Glu Asp Ser Gln Pro Gly Met Ser Gly Asn
Ser His Thr Ile Thr
```

-continued

| Glu | Asp | Ser | Lys | Pro | Ser | Gln | Glu | Asp | Glu | Val | Ile | Ile | Gly | Gly | Gln |
| Gly | Gln | Val | Ile | Asp | Phe | Thr | Glu | Asp | Thr | Gln | Ser | Gly | Met | Ser | Gly |
| Asp | Asn | Ser | His | Thr | Asp | Gly | Thr | Val | Leu | Glu | | | | | |

| Glu | Asp | Ser | Lys | Pro | Ser | Gln | Glu | Asp | Glu | Val | Ile | Ile | Gly | Gly | Gln |
| Gly | Gln | Val | Ile | Asp | Phe | Thr | Glu | Asp | Thr | Gln | Thr | Gly | Met | Ser | Gly | and

| Glu | Glu | Thr | Leu | Pro | Thr | Glu | Gln | Gly | Gln | Ser | Gly | Ser | Thr | Thr | Glu |
| Val | Glu | Asp | Thr | Lys | Gly | Pro | Glu | Val | Ile | Ile | Gly | Gly | Gln | Gly | Glu |
| Ile | Val | Asp | Ile | | | | | | | | | | | | |

| Glu | Glu | Asn | Leu | pro | Thr | Glu | Gln | Gly | Gln | Ser | Gly | Ser | Thr | Thr | Glu |
| Val | Glu | Asp | Thr | Lys | Gly | pro | Glu | Val | Ile | Ile | Gly | Gly | Gln | Gly | Glu |
| Val | Val | Asp | Ile | | | | | | | | | | | | |

| Glu | Glu | Ser | Leu | Pro | Thr | Glu | Gln | Gly | Gln | Ser | Gly | Gly | Ser | Thr | Thr |
| Glu | Val | Glu | Asp, | | | | | | | | | | | | | respectively.

The present fibronectin binding proteins can be used in immunization, whereby the proteins, preferably in combination with a fusion protein in order to form a larger antigen to react upon, are injected in doses creating an immunological reaction in the host mammal. Thus the fibronectin binding proteins can be used in vaccination of rumens to mastitis created by streptococcal infections.

Further, the fibronectin binding proteins can be used to block an infection in an open skin lesion. Wounds can be treated by using a suspension comprising the fibronectin binding protein. Thus the fibronectin binding proteins can be used to treat wounds, e.g., for blocking bacterial binding sites in fibronectin, or for immunization (vaccination). In the latter case the host produces specific antibodies which can protect against attachment by bacterial strains comprising such fibronectin binding proteins. Hereby the antibodies block the adherence of the bacterial strains to damaged tissue.

Examples of colonizing of tissue damage are:
a) colonizing of wounds in skin and connective tissue, which wounds have been caused by a mechanical trauma, chemical damage, and/or thermical damage;
b) colonizing of wounds on mucous membranes such as in the mouth cavity, or in the mammary glands, urethra or vagina;
c) colonizing of connective tissue proteins, which have been exposed by minimal tissue damage (micro lesions) in connection with epithelium and endothelium (mastitis, heart valve infection, hip exchange surgery).

When using the present fibronectin binding proteins, prepared by means of hybrid-DNA technique, or synthesized, for immunization (vaccination) in mammals, including humans, the proteins, or polypeptides are dispersed in sterile isotonic saline solution, optionally while adding a pharmaceutically acceptable dispersing agent. Different types of adjuvants can further be used in order to sustain the release in the tissue, and thus expose the protein for a longer period of time to the immuno defence system of a body.

A suitable dose to obtain immunization is 0.5 to 5 µg of fibronectin binding protein per kg body weight and injection at immunization. In order to obtain durable immunization, vaccinations should be carried out at consecutive occasions with an interval of 1 to 3 weeks, preferably at three occasions. Adjuvants are normally not added when repeating the immunization treatment.

When using the present fibronectin binding proteins or polypeptides for local topical administration the protein is dispersed in an isotonic saline solution to a concentration of 25 to 250 µg per ml. The wounds are then treated with such an amount only to obtain a complete wetting of the wound surface. For an average wound thus only a couple of milliliters of solution are used in this way. After treatment using the protein solution the wounds are suitably washed with isotonic saline solution or another suitable wound treatment solution.

Further the fibronectin binding protein, or synthetized polypeptide of the present invention can be used to diagnoze bacterial infections caused by *S. dysgalactiae* strains, whereby a fibronectin binding protein of the present invention is immobilized on a solid carrier, such as small latex or Sepharose[R] beads, whereupon sera containing antibodies are allowed to pass and react with the fibronectin binding protein thus immobilized. The agglutination is then measured by known methods.

Further the fibronectin binding protein or polypeptide can be used in an ELISA test (Enzyme Linked Immuno Sorbent Assay; E Engvall, Med. Biol. 55, 193 (1977)). Hereby wells in a polystyrene microtitre plate are coated with the fibronectin binding protein and incubated over night at 4° C. The plates are then thoroughly washed using PBS containing 0.05% Tween 20, and dried. Serial dilutions of the patient serum made in PBS-Tween, are added to the wells, and are incubated at 30° C. for 1.5 hrs. After rinsing anti-human IgG conjugated with an enzyme, or a horseradish peroxidase, or an alkaline phosphatase is added to the wells and further incubated at 30° C. for 1.5 hrs. During these incubations IgG from patient serum, and added antihuman IgG-enzyme conjugate, respectively, has been bound thereto. After rinsing, an enzyme substrate is added, p-nitrophosphate in case of an alkaline phosphatase, or orthophenylene diamine substrate (OPD) in case a peroxidase has been used, respectively. The wells of the plates are then rinsed using a citrate buffer containing 0.055% OPD, and 0.005% $H_2O_2$, and incubated at 30° C. for 10 min. The enzyme reaction is stopped by adding a 4N solution of $H_2SO_4$ to each well. The colour development is measured using a spectrophotometer.

Depending on the type of enzyme substrate used a fluorescence measurement can be used as well.

Another method to diagnoze *S. dysgalactiae* infections is by using the DNA gene probe method based on the nucleotide sequence for the fibronectin binding protein or part thereof. Thereby the natural or synthetic DNA sequence is attached to a solid carrier, such as a nitrocellulose filter, a nylon filter, or a polystyrene plate as mentioned above, by e.g., adding a milk in the case of diagnozing a mastitis, to the surface. The DNA gene probe, optionally labelled enzymatically, or by a radioactive isotope, is then added to the solid surface plate comprising the DNA sequence, whereby the DNA gene probe attaches to the membrane associated sequence where appearing. The enzyme or radioactive isotope can readily be determined by known methods.

Above the term fibronectin binding protein includes any of the polypeptide sequences as well, which constitute the minimal fibronectin binding site of the complete protein.

LEGENDS TO THE FIGURES

FIG. 1 Restriction map

A. Restriction map of the clone.

B. Different subclones constructed to determine the region in the gene which codes for fibronectin binding activity. The binding activity of the different gene products have been indicated.

C. Subclones obtained after digestion with ExoIII of pSDF102, and pSDF203, respectively. Scale: 1 cm=100 bp. M is the part of the DNA sequence which encodes the membrane associated part of the protein (=COOH-terminal). Subclone p102c10 contains the 3' end of the gene (FIG. 1a). $A_1$, $A_2$ och $A_3$, and $B_1$, $B_2$, and $B_3$, respectively, denote repetitive domains of the sequences (cf. FIG. 3)

Binding of $^{125}I$ labelled fibronectin to cells of *S. dysgalactiae* S2, and *S. aureus* Cowan I, respectively, at the addition of lysates of *E. coli*-clones. The percentage values given are related to the binding of $^{125}I$ labelled fibronectin to cells in the absence of Lysate. As a negative control a lysate of *E. coli* TG1 with pUC18-vector without insert was used, which had no influence on the binding of the cells to fibronectin. *E. coli* clone 015 contains a gene from *S. aureus* encoding for fibronectin binding activity.

References

1. Hymes, R. O. (1985) Annu. Rev. Cell Biol. 1, 67–90.
2. Kuusela, P. (1978) Nature 276, 718–720.
3. Switalski, L. et al (1982) Eur. J. Clin. Microbiol. 1, 381–387.
4. Fröman, G. et al. (1984) J. Biol. Chem. 259, 14899–14905.
5. Baloda, S. B. et al (1985) FEMS Microbiol. Lett. 28, 1–5.
6. Wadström, T. et al (1985) In Jackson, G. J. (ed), Pathogenesis of Infection, Springer Verlag, Berlin, Heidelberg, New York, Tokyo, pp. 193–207.
7. Lopes, J. D. et al (1985) Science 229, 275–277.
8. Langone, I. L (1982) Adv. Immunol. 32, 157–252.
9. Marmur, J. (1961) J. Mol. Biol. 3, 208–218.
10. Flock, J.-I. et al (1987) The EMBO Journal 6, 2351–2357.
11. Monstein, H.-J. et al (1986) Biochem. Int. 12, 889–896.

We claim:

1. A fibronectin binding protein or polypeptide comprising one or more amino acid sequences selected from the group consisting of Glu Asp Thr Gln Thr Ser Gln Glu Asp Ile Val Leu Gly Gly Pro Gly
Gln Val Ile Asp Phe Thr Glu Asp Ser Gln Pro Gly Met Ser Gly Asn
Ser His Thr Ile Thr Glu Asp Ser Lys Pro Ser Gln Glu Asp Glu Val Ile Ile Gly Gly Gln
Gly Gln Val Ile Asp Phe Thr Glu Asp Thr Gln Ser Gly Met Ser Gly
Asp Asn Ser His Thr Asp Gly Thr Val Leu Glu Glu Asp Ser Lys Pro Ser Gln Glu Asp Glu Val Ile Ile Gly Gly Gln
Gly Gln Val Ile Asp Phe Thr Glu Asp Thr Gln Thr Gly Met Ser Gly and Glu Glu Thr Leu Pro Thr Glu Gln Gly Gln Ser Gly Ser Thr Thr Glu
Val Glu Asp Thr Lys Gly Pro Glu Val Ile Ile Gly Gly Gln Gly Glu
Ile Val Asp Ile Glu Glu Asn Leu Pro Thr Glu Gln Gly Gln Ser Gly Ser Thr Thr Glu
Val Glu Asp Thr Lys Gly Pro Glu Val Ile Ile Gly Gly Gln Gly Glu
Val Val Asp Ile Glu Glu Ser Leu Pro Thr Glu Gln Gly Gln Ser Gly Gly Ser Thr Thr
Glu Val Glu Asp 2. The protein or polypeptide of claim 1, wherein the amino acid sequence comprises

| Glu | Asp | Thr | Gln | Thr | Ser | Gln | Glu | Asp | Ile | Val | Leu | Gly | Gly | Pro | Gly |
|-----|-----|-----|-----|-----|-----|-----|-----|-----|-----|-----|-----|-----|-----|-----|-----|
| Gln | Val | Ile | Asp | Phe | Thr | Glu | Asp | Ser | Gln | Pro | Gly | Met | Ser | Gly | Asn |
| Ser | His | Thr | Ile | Thr | | | | | | | | | | | |
| Glu | Asp | Ser | Lys | Pro | Ser | Gln | Glu | Asp | Glu | Val | Ile | Ile | Gly | Gly | Gln |
| Gly | Gln | Val | Ile | Asp | Phe | Thr | Glu | Asp | Thr | Gln | Ser | Gly | Met | Ser | Gly |
| Asp | Asn | Ser | His | Thr | Asp | Gly | Thr | Val | Leu | Glu | | | | | |

-continued

| Glu | Asp | Ser | Lys | Pro | Ser | Gln | Glu | Asp | Glu | Val | Ile | Ile | Gly | Gly | Gln |
| Gly | Gln | Val | Ile | Asp | Phe | Thr | Glu | Asp | Thr | Gln | Thr | Gly | Met | Ser | Gly. |

3. The protein or polypeptide of claim 1, wherein the amino acid sequence comprises

| Glu | Glu | Thr | Leu | Pro | Thr | Glu | Gln | Gly | Gln | Ser | Gly | Ser | Thr | Thr | Glu |
| Val | Glu | Asp | Thr | Lys | Gly | Pro | Glu | Val | Ile | Ile | Gly | Gly | Gln | Gly | Glu |
| Ile | Val | Asp | Ile | | | | | | | | | | | | |
| Glu | Glu | Asn | Leu | Pro | Thr | Glu | Gln | Gly | Gln | Ser | Gly | Ser | Thr | Thr | Glu |
| Val | Glu | Asp | Thr | Lys | Gly | Pro | Glu | Val | Ile | Ile | Gly | Gly | Gln | Gly | Glu |
| Val | Val | Asp | Ile | | | | | | | | | | | | |
| Glu | Glu | Ser | Leu | Pro | Thr | Glu | Gln | Gly | Gln | Ser | Gly | Gly | Ser | Thr | Thr |
| Glu | Val | Glu | Asp. | | | | | | | | | | | | |

Figure 4:
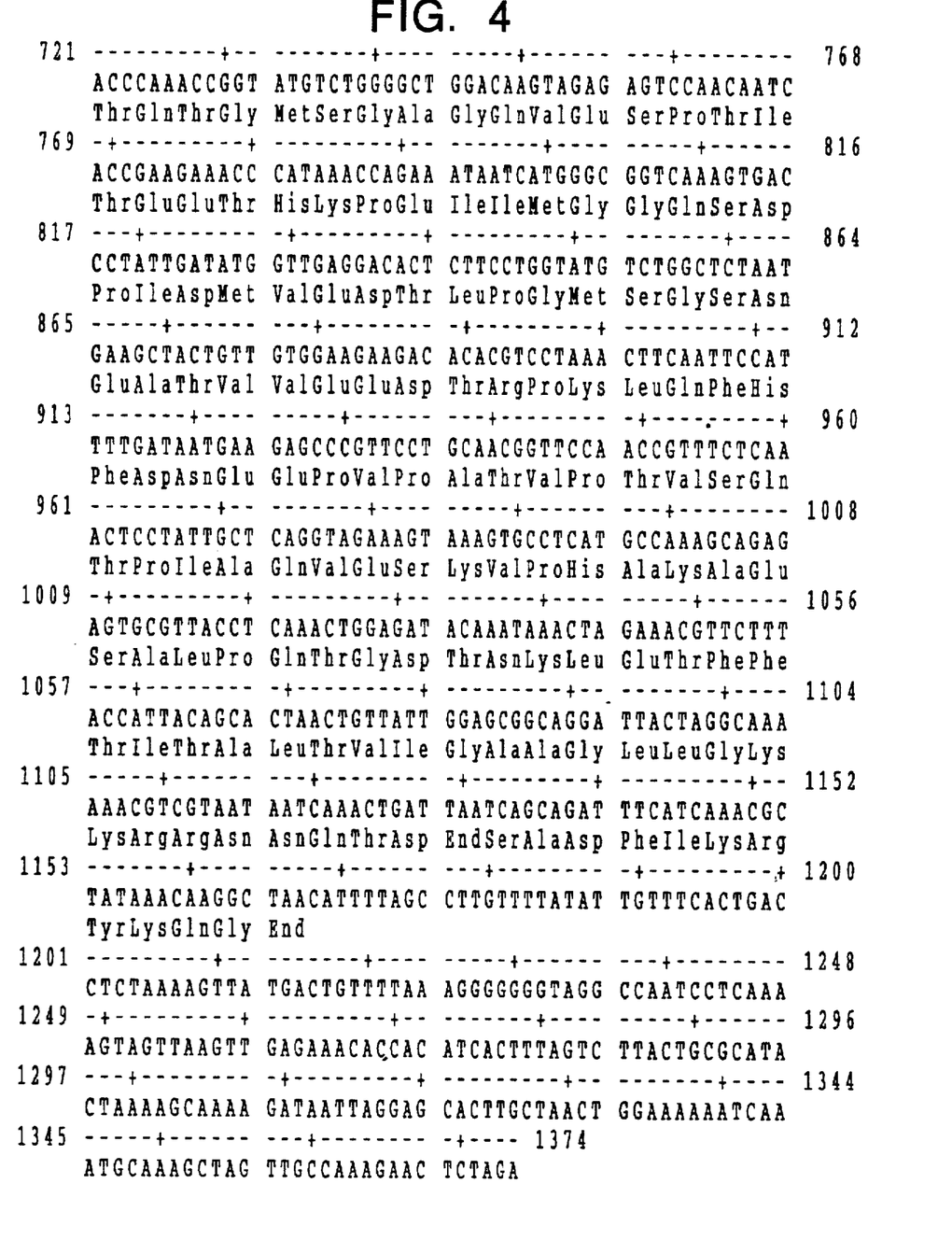
FIG. 4 shows the nucleotide and deducted amino acid sequences of pSDF102

4. The protein or polypeptide of claim 1, wherein the amino acid sequence comprises the amino acid sequence of FIG. 4.

region consists of one or more amino acid sequences selected from the group consisting of:

| Glu | Asp | Thr | Gln | Thr | Ser | Gln | Glu | Asp | Ile | Val | Leu | Gly | Gly | Pro | Gly |
| Gln | Val | Ile | Asp | Phe | Thr | Glu | Asp | Ser | Gln | Pro | Gly | Met | Ser | Gly | Asn |
| Ser | His | Thr | Ile | Thr | | | | | | | | | | | |
| Glu | Asp | Ser | Lys | Pro | Ser | Gln | Glu | Asp | Glu | Val | Ile | Ile | Gly | Gly | Gln |
| Gly | Gln | Val | Ile | Asp | Phe | Thr | Glu | Asp | Thr | Gln | Ser | Gly | Met | Ser | Gly |
| Asp | Asn | Ser | His | Thr | Asp | Gly | Thr | Val | Leu | Glu | | | | | |
| Glu | Asp | Ser | Lys | Pro | Ser | Gln | Glu | Asp | Glu | Val | Ile | Ile | Gly | Gly | Gln |
| Gly | Gln | Val | Ile | Asp | Phe | Thr | Glu | Asp | Thr | Gln | Thr | Gly | Met | Ser | Gly; |
| Glu | Glu | Thr | Leu | Pro | Thr | Glu | Gln | Gly | Gln | Ser | Gly | Ser | Thr | Thr | Glu |
| Val | Glu | Asp | Thr | Lys | Gly | Pro | Glu | Val | Ile | Ile | Gly | Gly | Gln | Gly | Glu |
| Ile | Val | Asp | Ile | | | | | | | | | | | | |
| Glu | Glu | Asn | Leu | Pro | Thr | Glu | Gln | Gly | Gln | Ser | Gly | Ser | Thr | Thr | Glu |
| Val | Glu | Asp | Thr | Lys | Gly | Pro | Glu | Val | Ile | Ile | Gly | Gly | Gln | Gly | Glu |
| Val | Val | Asp | Ile | | | | | | | | | | | | |
| Glu | Glu | Ser | Leu | Pro | Thr | Glu | Gln | Gly | Gln | Ser | Gly | Gly | Ser | Thr | Thr |
| Glu | Val | Glu | Asp; | | | | | | | | | | | | |

Figure 5:
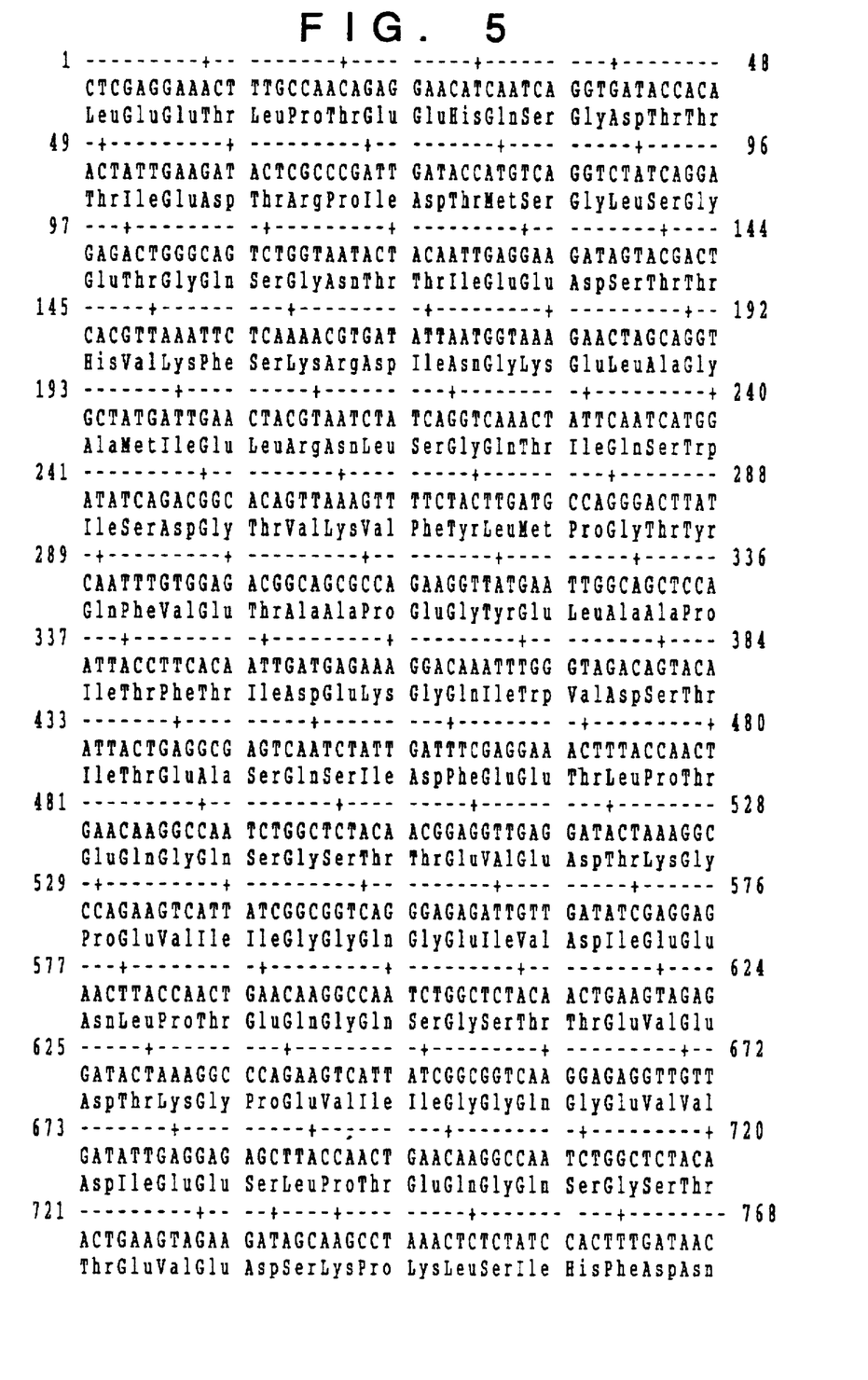
FIG. 5 shows the nucleotide and deducted amino acid sequences of pSDF203

5. The protein or polypeptide of claim 1, wherein the amino acid sequence comprises the amino acid sequence of FIG. 5.

6. A fusion protein comprising the fibronectin binding protein of claim 1.

7. The fusion protein of claim 6, further comprising a natural carrier protein.

8. The fusion protein of claim 7, wherein the natural carrier protein is the IgG binding region of protein A.

9. A recombinant protein or polypeptide comprising a fibronectin binding region, wherein said fibronectin binding the amino acid sequence of FIG. 4; and the amino acid sequence of FIG. 5.

10. A chemical synthesis method for the preparation of a fibronectin binding protein or polypeptide according to claim 2, whereby an amino acid residue is formed based upon the nucleotide sequence encoding said protein or polypeptide starting from the C-terminal glycine which step by step is reacted with the appropriate amino acid, whereby it is finally reacted with glutamic acid at the N-terminal end to result in the formation of a fibronectin binding protein or polypeptide.

11. A recombinant protein or polypeptide according claim 9, wherein said recombinant protein or polypeptide is encoded by one or more nucleotide sequences selected from the group consisting of

```
CTA GAT ACC TCA GAA AAC AAA AAA TCT GTA ACT GAA AAA GTA ATA ACT
AGC GAT GTT AAA TAT AAG ATT AAT GAT AAA GAA GTG AAA GGT AAA GAA
CTA GAC GAT GTC TCT TTA ACT TAC AGT AAA GAA ACC GTT CGT AAG CCA
CAG GTG GAA CCA AAT GTT CCT GAT ACA CCT GGA GAA AAA CCA TTG ACA
CCG CTT GCA CCG TCA GAA CCT TCA CAA CCA TCT ATT CCA GAG ACA CCA
CTG ATA CCG TCA GAA CCT TCA GTT CCA GAG ACA TCA ACA CCA GAA GGT
CCA ACA GAG GGA GAA AAT AAT CTT GGT GGT CAG AGT GAA GAG ATA ACG
ATT ACA GAA GAT TCT CAA TCA GGG ATG TCT GGT CAA AAT CCT GGT TCT
GGA AAT GAA ACA GTG GTT

GAA GAC ACT CAA ACA AGT CAA GAG GAT ATT GTA CTT GGT GGT CCA GGT
CAA GTG ATT GAC TTT ACA GAA GAT AGC CAA CCG GGT ATG TCT GGT AAT
AAT AGC CAT ACT ATT ACA

GAA GAT TCT AAA CCA AGT CAA GAG GAT GAG GTG ATA ATC GGC GGT CAA
GGT CAG GTG ATT GAC TTT ACA GAA GAT ACT CAA TCT GGT ATG TCT GGG
GAT AAT AGC CAT ACA GAT GGG ACA GTG CTT GA

-continued

```
GAG GAG AAC TTA CCA ACT GAA CAA GGC CAA TCT GGC TCT ACA ACT GAA
GTA GAG GAT ACT AAA GGC CCA GAA GTC ATT ATC GGC GGT CAA GGA GAG
GTT GTT GAT ATT

GAG GAG AGC TTA CCA ACT GAA CAA GGC CAA TCT GGC TCT ACA ACT GAA
GTA GAA GAT.
```

12. The recombinant protein or polypeptide according to claim 9, produced by a process wherein
   a) at least one hybrid DNA molecule encoding said protein or polypeptide is cloned into a microorganism;
   b) the microorganism is cultivated in a growth promoting medium;
   c) the cloned microorganism is lysed; and
   d) the protein or polypeptide is recovered.

13. A chemical synthesis method for the preparation of a fibronectin binding protein or polypeptide according to claim 3, whereby an amino acid residue is formed based upon the nucleotide sequence encoding said protein or polypeptide starting from the C-terminal aspartic acid which step by step is reacted with the appropriate amino acid, whereby it is finally reacted with glutamic acid at the N-terminal end to result in the formation of a fibronectin binding protein or polypeptide.

* * * * *